United States Patent

Thornton

Patent Number: 5,566,683
Date of Patent: Oct. 22, 1996

[54] APPARATUS FOR PREVENTION OF SNORING AND IMPROVED BREATHING DURING SLEEP

[76] Inventor: W. Keith Thornton, 5524 Edlen, Dallas, Tex. 75220

[21] Appl. No.: 410,325

[22] Filed: Mar. 24, 1995

Related U.S. Application Data

[63] Continuation-in-part of Ser. No. 129,598, Sep. 29, 1993, Pat. No. 5,427,117.

[51] Int. Cl.$^6$ ............................................. A61C 5/00
[52] U.S. Cl. .................................... 128/848; 128/859
[58] Field of Search .................................. 128/848, 859, 128/860, 861, 862; 602/902; 433/36, 37, 38, 41, 43, 48

[56] References Cited

U.S. PATENT DOCUMENTS

| | | |
|---|---|---|
| 746,869 | 12/1903 | Moulton . |
| 1,076,534 | 12/1913 | Wallen . |
| 1,146,264 | 7/1915 | Kelly . |
| 1,649,664 | 11/1927 | Carter . |
| 1,674,336 | 6/1928 | King . |
| 2,171,695 | 9/1939 | Harper . |
| 2,424,533 | 7/1947 | Faires ........................... 128/136 |
| 2,521,039 | 9/1950 | Carpenter ..................... 128/136 |
| 2,531,222 | 11/1950 | Kesling ........................... 32/14 |
| 2,590,118 | 3/1952 | Oddo, Jr. ...................... 128/136 |
| 2,833,278 | 5/1958 | Ross ............................. 128/136 |
| 2,882,893 | 4/1959 | Godfroy ....................... 128/136 |
| 3,107,668 | 10/1963 | Thompson .................... 128/136 |
| 3,124,129 | 3/1964 | Grossberg .................... 128/136 |
| 3,321,832 | 5/1967 | Weisberg ........................ 32/32 |
| 3,434,470 | 3/1969 | Strickland .................... 128/136 |
| 3,457,916 | 7/1969 | Wolicki ........................ 128/136 |
| 3,513,838 | 5/1970 | Foderick et al. ............. 128/861 |
| 3,864,832 | 2/1975 | Carlson et al. .............. 128/136 |
| 3,871,370 | 3/1975 | McDonald ................... 128/136 |
| 4,016,650 | 4/1977 | Leusner et al. ................. 32/17 |
| 4,026,024 | 5/1977 | Tradowsky ..................... 32/19 |
| 4,114,614 | 9/1978 | Kesling ....................... 128/136 |
| 4,182,312 | 1/1980 | Mushabac ...................... 433/68 |
| 4,227,877 | 10/1980 | Tureaud et al. ................ 433/37 |
| 4,304,227 | 12/1981 | Samelson ..................... 128/136 |
| 4,376,628 | 3/1983 | Aardse .......................... 433/80 |
| 4,439,147 | 3/1984 | Magill et al. .................... 433/3 |
| 4,495,945 | 1/1985 | Leigner ..................... 128/200.26 |
| 4,505,672 | 3/1985 | Kurz ................................ 433/6 |
| 4,553,549 | 11/1985 | Pope et al. .................... 128/421 |
| 4,568,280 | 2/1986 | Ahlin ............................... 433/6 |
| 4,569,342 | 2/1986 | von Nostitz .................. 128/136 |
| 4,593,686 | 6/1986 | Lloyd et al. .................. 128/136 |
| 4,602,905 | 7/1986 | O'Keefe, III ................... 433/41 |
| 4,639,220 | 1/1987 | Nara et al. ...................... 433/69 |
| 4,773,853 | 9/1988 | Kussick et al. ................... 433/6 |
| 4,799,500 | 1/1989 | Newbury ...................... 128/859 |
| 4,862,903 | 9/1989 | Campbell ..................... 128/861 |
| 4,901,737 | 2/1990 | Toone .......................... 128/848 |
| 4,932,867 | 6/1990 | Ueno ............................. 433/69 |
| 4,955,393 | 9/1990 | Adell ........................... 128/859 |
| 5,003,994 | 4/1991 | Cook ............................ 128/848 |
| 5,018,533 | 5/1991 | Hawkins ....................... 128/848 |
| 5,028,232 | 7/1991 | Snow ............................. 433/24 |
| 5,042,506 | 8/1991 | Liberati ........................ 128/848 |
| 5,056,534 | 10/1991 | Wright ......................... 128/848 |
| 5,078,600 | 1/1992 | Austin ............................ 433/73 |
| 5,092,346 | 3/1992 | Hays et al. ................... 128/848 |
| 5,103,838 | 4/1992 | Yousif .......................... 128/859 |
| 5,117,816 | 6/1992 | Shapiro et al. ............ 128/200.24 |
| 5,154,609 | 10/1992 | George .......................... 433/68 |
| 5,183,057 | 2/1993 | Syrop et al. .................. 128/845 |
| 5,188,529 | 2/1993 | Luth .............................. 433/68 |
| 5,267,862 | 12/1993 | Parker ......................... 433/215 |
| 5,277,202 | 1/1994 | Hays ............................ 128/848 |
| 5,313,960 | 5/1994 | Tomasi ........................ 128/848 |

FOREIGN PATENT DOCUMENTS

| | | |
|---|---|---|
| 0312368 | 4/1989 | European Pat. Off. . |
| 0359135 | 3/1990 | European Pat. Off. . |
| 2320501 | 11/1974 | Germany . |
| 1569129 | 6/1980 | United Kingdom . |

*Primary Examiner*—Sam Rimell
*Attorney, Agent, or Firm*—Baker & Botts, L.L.P.

[57] ABSTRACT

A dental device is provided in which a post extends downward from an upper arch to cause a lower arch to extend forward, thereby causing a user's lower jaw to extend forward.

22 Claims, 3 Drawing Sheets

5,566,683

APPARATUS FOR PREVENTION OF SNORING AND IMPROVED BREATHING DURING SLEEP

RELATED APPLICATIONS

This application is a continuation-in-part of U.S. patent application Ser. No. 08/129,598, filed on Sep. 29, 1993, for "Apparatus for Prevention of Snoring and Improved Breathing During Sleep," now U.S. Pat. No. 5,427,117, herein incorporated by reference.

TECHNICAL FIELD OF THE INVENTION

This invention relates generally to medical and dental devices, and more particularly to an apparatus for prevention of snoring and improved breathing during sleep.

BACKGROUND OF THE INVENTION

Snoring is a problem that plagues millions of people. And snoring not affects not only the snorer, but also those within earshot of the snorer. Consequently, many attempts have been made to solve the snoring problem.

For example, U.S. Pat. No. 5,117,816 issued to Shapiro, et al., discloses an anti-snoring device that uses a single upper mouth piece with a flange extending downward to maintain the lower jaw in a forward position. Such devices are referred to as one-piece devices. The Shapiro, et al. Device takes advantage of the known technique of extending the lower jaw of a snorer, thereby opening the air passage and reducing or preventing snoring. Similar devices have also been disclosed in U.S. Pat. No. 5,003,994 issued to Cook, and U.S. Pat. No. 5,092,346, issued to Hays, et al.

The amount of forward extension of the lower jaw that is most effective at reducing or eliminating snoring varies from person to person. In prior art devices, the amount of forward adjustment is fixed, and thus cannot be adjusted by the user to increase the effectiveness of the device or to increase comfort. Therefore, a need has arisen for a device that allows for adjustment of the forward extension of the lower jaw in an anti-snoring device.

SUMMARY OF THE INVENTION

In accordance with the teachings of the present invention, a dental device is provided which substantially eliminates or reduces disadvantages and problems associated prior art anti-snoring devices. In particular, a dental device is provided in which an upper arch fits at least some of a user's upper teeth, the upper arch including a slot. A post extends downward from the upper arch, and includes a base adapted to fit in the slot. The base also includes a plurality of receiving grooves. A ramp is adapted to fit in at least one of the receiving grooves, and causes the user's lower jaw to extend forward with respect to the user. The receiving grooves are oriented such that the amount of forward extension of the user's lower jaw depends on which receiving groove or grooves the ramp fits in. In other particular embodiments, the forward position of the post can be adjusted by using one or more shims, or through the use of a set screw.

In a preferred embodiment, a lower arch is provided, and the post contacts the lower arch directly, or indirectly by contacting attachments to the lower arch.

Also provided is a dental device in which an upper arch fits at least some of the user's upper teeth, with the arch including a slot. A base is adapted to fit in the slot, and the base includes a drive member. A ramp is coupled to the drive member and extends downward from the upper arch. The drive member adjusts the position of the ramp, and the ramp causes the user's lower jaw to extend forward with respect to the user.

An important technical advantage of the present invention is the fact that the forward location of a user's lower jaw can be adjusted by adjusting a post which extends downward from the upper arch. The ability to adjust the forward position of the downwardly extending post allows the user to determine the most effective and comfortable amount of forward extension of the lower jaw.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
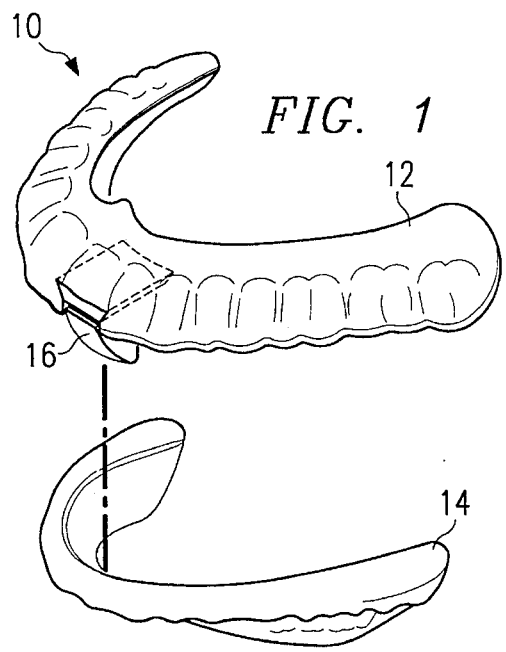
FIG. 1 illustrates an embodiment of an anti-snoring device constructed according to the teachings of the present invention.

FIG. 1 illustrates an isometric view of an anti-snoring device 10 constructed according to the teachings of the present invention. As shown in FIG. 1, anti-snoring device 10 includes an upper arch 12 and a lower arch 14. Arches 12 and 14 fit at least some of a user's upper and lower arches of teeth, respectively. Extending from upper arch 12 is a post 16. As shown in FIG. 1, post 16 slides into a slot in the front-center of upper arch 12. Post 16, when in use, makes contact with the inside surface of lower arch 14. This contact causes lower arch 14, and consequently a user's lower jaw, to extend slightly forward. Forward extension of the lower jaw allows the air passage of the user to remain open, thereby preventing snoring and improving breathing during sleep.

Pose 16 may have a wide range of shapes, including various lengths, depths, and widths, to perform this function. The term "post" is used to describe any such structure. Furthermore, post 16 may directly contact the lower arch 14, or it may contact an attachment to lower arch 14, such as a stop, an adjustable stop, any attachment extending upward, or any other attachment to lower arch 14.

As will be discussed below, the position of post 16 is adjustable so as to allow adjustment of the amount of forward extension of the user's lower jaw. As can be seen in FIG. 1, and will be shown in detail in FIG. 3, the surface of post 16 which contacts lower arch 14 is preferably curved so as to allow for more comfortable forward extension of the lower jaw. In particular, the post is curved so as to account for Christensen's phenomenon. With Christensen's phenomenon, extension of the lower jaw (the mandible) forward causes a gap or separation in the molar region of the upper and lower jaws.

Figure 2:
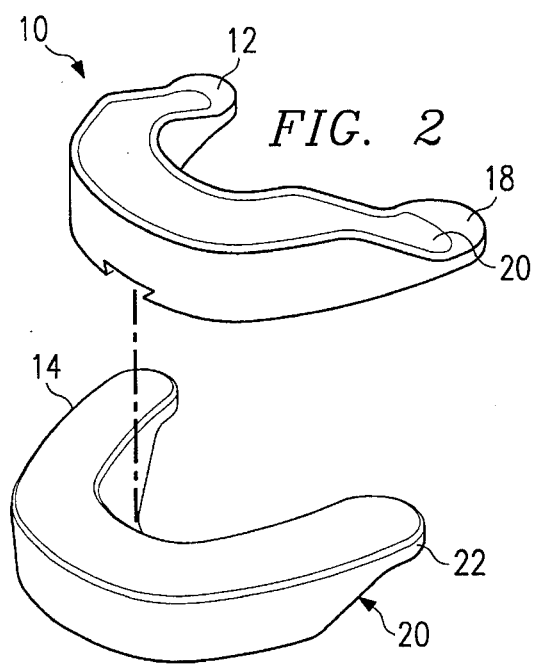
FIG. 2 illustrates another embodiment of an anti-snoring device constructed according to the teachings of the present invention.

FIG. 2 illustrates an alternative embodiment of the present invention in which upper arch 12 includes a tray 18 filled with a deformable material 20. Tray 18 (as well as arches 12 and 14 of FIG. 1) may be made from any material suitable for dental uses, such as methylmethacrylate or a polycarbonate resin thermoplastic such as that sold under the Registered Trademark Lexan. Such materials are known to those familiar with dental mouthpieces, and other materials may be used without departing from the intended scope herein. Deformable material 20 is bonded to tray 18 and used for custom forming of a mold of the user's teeth for proper fitting during use. By using deformable material 20, each user can customize his or her anti-snoring device without the expense associated with having a dental mold prepared by a dental professional.

A suitable material for deformable material 20 is the ethylene-vinyl acetate copolymer resin sold under the Registered Trademark Elvax. Any other suitable deformable materials may also be used. Typically, with a material such as Elvax, the material 20 is heated to a temperature of about 150 Fahrenheit, through a microwave oven or by heating in hot water, for example, so as to place the material 20 in its deformable state. A user then inserts the arch 12 and bites down, thereby deforming the material 20 into the shape of the user's upper arch of teeth. The upper arch 12 is then removed and allowed to cool, thereby setting the material 20 into a mold of the user's upper arch.

Likewise, lower arch 14 includes a tray 22 filled with a deformable material 20. A mold of the lower arch of teeth is formed as described above in connection with upper arch 12.

Figure 3:
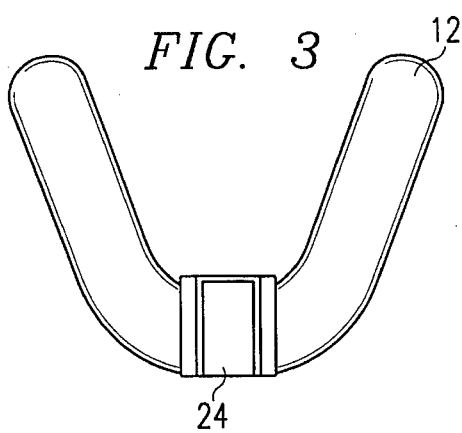
FIG. 3 illustrates a bottom view of a particular embodiment of an upper arch constructed according to the teachings of the present invention.

FIG. 3 illustrates a bottom view of a particular embodiment of upper arch 12. The view of FIG. 3 applies to both embodiments shown in FIGS. 1 and 2. As shown in FIG. 3, a slot 24 is provided for insertion of post 16. Slot 24, in a particular embodiment, is dove-tailed to allow for insertion of a dove-tailed post 16.

Figure 4A:
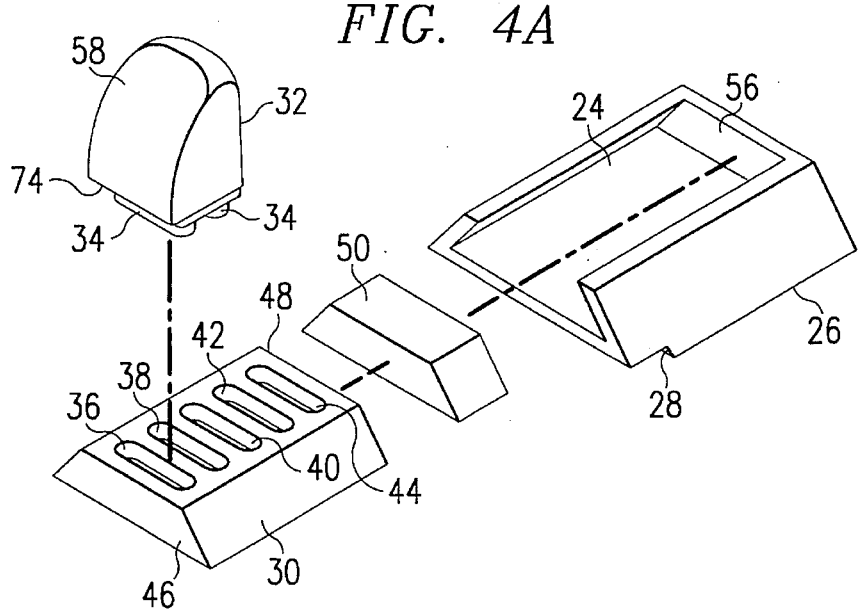
FIGS. 4A and 4B illustrate particular embodiments of apparatus for adjustment of the forward extension of the lower jaw according to the teachings of the present invention.

As shown in FIG. 4A, the slot 24 discussed in connection with FIG. 3 may be formed by joining a receiving member 26 to the upper arch 12. Because dental labs are familiar with forming upper arch molds, it is convenient to separately form receiving member 26 and join it to such an upper arch mold, for example by bonding it to the upper arch 12. However, no receiving member 26 need be provided, and the slot 24 may be formed integrally with upper arch 12. Receiving member 26 may include a shoulder 28 to assist in joining the receiving member 26 to the upper arch 12.

Figure 5:
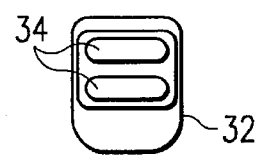
FIG. 5 illustrates a bottom view of a particular embodiment of a ramp member constructed according to the teachings of the present invention.

As shown in FIG. 4A, the post 16 may include a base 30 and ramp member 32. The base 30 is formed to matchingly fit within slot 24, and in the particular embodiment shown is dove-tailed to fit within slot 24. Ramp member 32 includes feet (or a single foot) 34 for insertion into one or more receiving grooves 36–44. FIG. 5 illustrates a bottom view of a particular embodiment of ramp member 32 of post 16. The ramp 32, base 30, and receiving member 26 may be formed of any suitable material, and typically will be formed of an acrylic.

The particular location of ramp 32 can be adjusted by moving it between different receiving grooves 36–44. Thus, in the particular embodiment shown, with five receiving grooves, and two feet 34 on ramp member 32, four different positions are available for ramp member 32. Furthermore, by making the distance from receiving groove 36 to an end 46 of base 30 different from the distance between receiving groove 44 and an end 48 of base 30, four additional positions are available for ramp member 32 by inserting end 46 into slot 24 (rather than end 48).

When the base 30 is turned, such that end 46 is inserted within slot 26, the ramp 32 is maintained in the orientation shown in FIG. 4A such that curved surface 58 contacts lower arch 14 (or any attachment to lower arch 14). As discussed above, curved surface 58 is curved to match the movement of the lower jaw as defined by Christensen's phenomenon.

It is possible for a user to adjust the location of ramp member 32, and therefore the forward extension of the lower jaw, by moving the ramp 32 from receiving groove to receiving groove. However, during use, the forces exerted on the ramp 32 may be sufficient to dislodge it from the receiving grooves 36–44. Therefore, ramp member 32, after placing it in the appropriate receiving grooves, is preferably bonded to the base 30.

For a user to adjust the forward location of the lower jaw, several posts, each post comprising a combination of base 30 and ramp 32, can be provided, with the location of ramp 32 on each post being different. The user can then try each of the posts by inserting each one into slot 24, until the most effective and comfortable one is found.

It should be understood that the receiving grooves 36–44 need not be included, and the base 30 and ramp member 32 may be formed as one piece or may be joined with other techniques than receiving grooves and feet. Furthermore, the number of receiving grooves shown in the various FIGUREs is exemplary only, and other numbers of grooves may be used without departing from the intended scope herein.

Another alternative for adjusting the position of the post 16 involves the use of one or more shims, such as shim 50 shown in FIG. 4. Shim 50 is formed to match the slot 24, and in the particular embodiment shown is beveled to dove-tail within slot 24. In a particular embodiment, the base 30 may be 9 millimeters long and one or more shims of 1 to 3 millimeters each can be inserted within the slot 24 to adjust the relative position of the post 16.

Figure 4B:
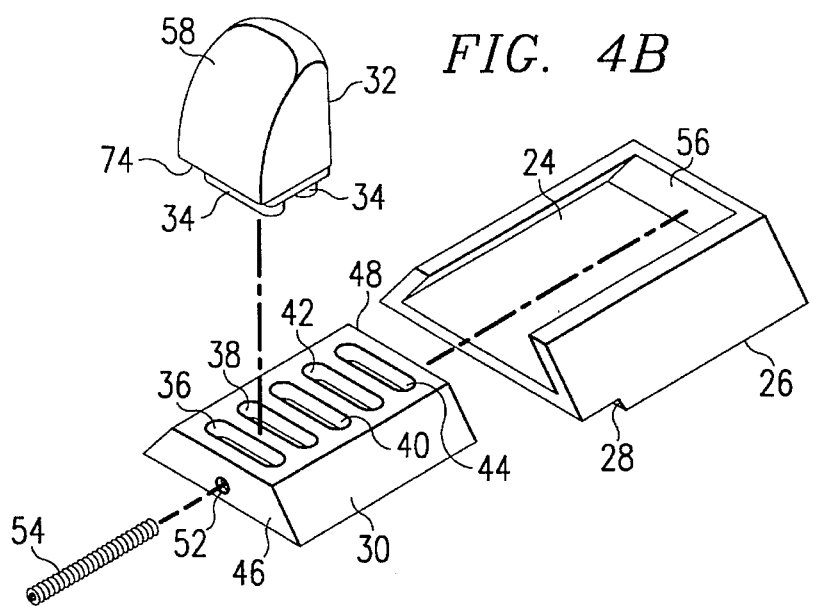

As another adjustment alternative, as shown in FIG. 4B, a threaded hole 52 can be provided through base 30. A set screw 54 is disposed within the threaded hole 52. The end of set screw 54 opposite stop 56 is adapted to receive a turning tool, such as a screwdriver or allen wrench. Such a tool can be inserted within hole 52 and used to turn the set screw so as to move the relative position of post 16 within receiving member 26.

The particular embodiments shown in FIGS. 4A and 4B are exemplary only, and other techniques may be used to adjust the forward location of the post 16 without departing from the intended scope of the present invention. Furthermore, the term "post" is used herein to generally describe any member extending from the upper arch 12 to cause forward extension of the lower jaw. Thus, the term "post" refers to the combination of base 30 and ramp 32, as well as the ramp 32 alone, or any other member that extends from the upper arch 12 to contact the lower arch 14, or to contact any attachment to the lower arch 14, to cause forward extension of the user's lower jaw.

Figure 6:
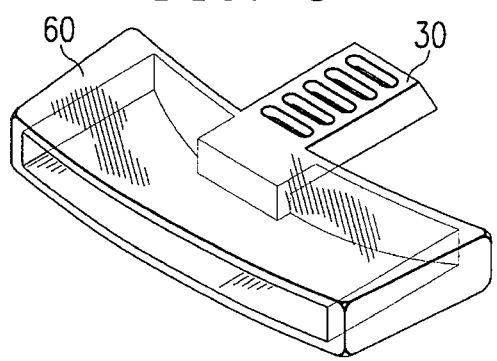
FIG. 6 illustrates a particular embodiment of a breathing beak constructed according to the teachings of the present invention.

FIG. 6 illustrates a particular embodiment of a breathing beak 60 coupled to a base 30. Breathing beak 60 includes breathing channels to allow air to pass between the user's lips while sleeping. This ability to allow air to pass through the user's mouth increases the effectiveness of the anti-snoring device of the present invention, by allowing more air to pass into the breathing passageway during sleep. The particular embodiment shown in FIG. 6 is exemplary only, and other breathing channels coupled to the upper arch 12 or the lower arch 14 may be used without departing from the intended scope herein.

Figure 7:
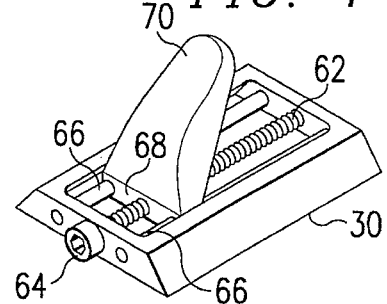
FIG. 7 illustrates another embodiment of an adjustable post constructed according to the teachings of the present invention.

FIG. 7 illustrates another embodiment of a base 30 for insertion into slot 24. As shown in FIG. 7, base 30 includes threaded drive 62. Threaded drive 62 includes a head 64 to facilitate rotation, and may be suitable for mating with a driving tool such as an allen wrench or screwdriver. Base 30 of FIG. 7 also includes guide rods 66. Guide rods 66 and threaded drive 62 pass through a ramp base 68. Ramp base 68 is coupled to or formed integrally with ramp 70. In a particular embodiment, ramp 70 is formed of an acrylic such as methylmethacrylate, while the remaining components of FIG. 7 are formed of metal, such as stainless steel. However, other suitable materials may also be used without departing from the intended scope herein.

With the embodiment shown in FIG. 7, the location of ramp 70 can be adjusted by turning the threaded drive 62 through the use of head 64. Furthermore, threaded drive 62 can be coupled to a motorized drive mechanism, to allow for electronic control of the relative location of ramp 70. This coupling to a motor for electronic control can be performed in a clinical setting, so as to clinically identify the most effective position of ramp 70, or it can be used in the home setting, by the user or the user's companion to set the ramp to the most comfortable and effective position.

The particular drive mechanism shown in FIG. 7 (the drive 62) is exemplary only, and other drive members can be used without departing from the intended scope herein. Furthermore, no base need be included, and any such drive member can be formed integrally or otherwise with the upper arch 12.

It should be understood that the adjustment of the position of the user's lower jaw can be accomplished by using an adjustable stop or other attachment on the lower arch 14, for contact with a fixed or adjustable post extending from the upper arch. The adjustment of any such lower arch stop or attachment can be accomplished in ways similarly to those described in connection with the previous FIGUREs, as well as with other structures.

An important technical advantage of the present invention is the fact that the forward location of the user's lower jaw is adjustable by changing the position of the post. The ability to change the position of the post allows users to adjust the effectiveness and comfort of the anti-snoring device.

Figure 8:
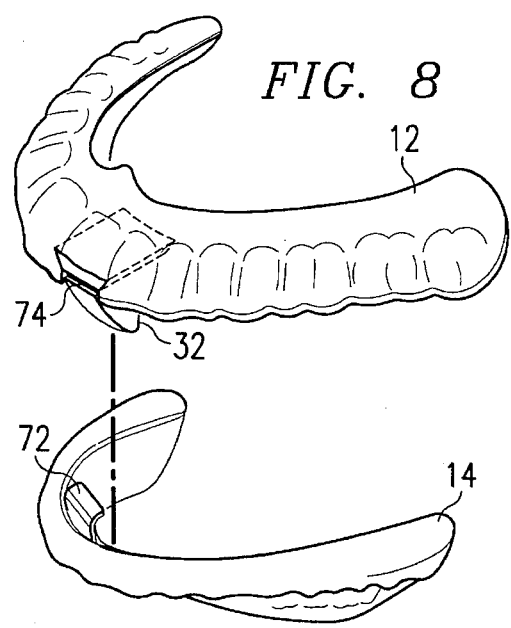
FIGS. 8 and 9 illustrate a particular embodiment of a locking tab constructed according to teachings of the present invention.
Figure 9:
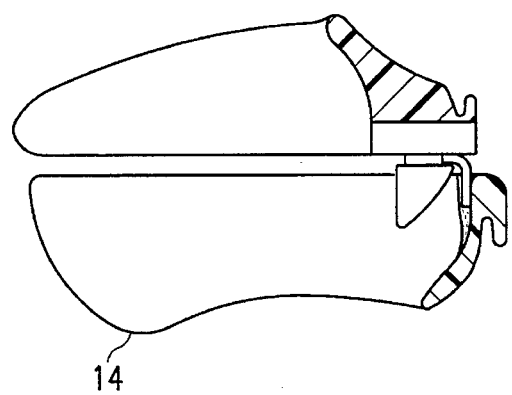

FIGS. 8 and 9 illustrate lower arch 14 with locking shoulder 72, which may be used with any of the embodiments described above. Locking shoulder 72 may be bonded to or formed integrally with lower arch 14, and engages with shoulder 74 of ramp 32. In a particular embodiment, locking shoulder 72 may be formed of metal, such as stainless steel, and bonded to lower arch 14. The engagement of the shoulders 32 and 74 prevents the user from lowering the lower jaw, unless the user disengages the shoulders by extending the lower jaw far enough forward to disengage the shoulders. By preventing the user's mouth from opening during sleep, the ramp member 32 will not disengage from the inside surface of the lower arch 14. It should be understood, however, that no locking shoulder 72 or ramp shoulder 74 need be included.

An important technical advantage of the present invention is the fact that side-to-side movement is not restricted during use, as the ramp member 32, even when engaged with shoulder 72, is not prohibited from sliding side-to-side. This freedom of side-to-side movement provides a significant advantage since it provides a more comfortable device for the user.

Although the present invention has been described in detail, it should be understood that various changes, modifications, or substitutions can be made without departing from the intended scope as defined by the appended claims.

What is claimed is:

1. A dental device, comprising:
   an upper arch fitting at least some of a user's upper teeth, said upper arch including a slot; and
   a post extending downward from said upper arch, said post including:
     a base adapted to fit in said slot, said base including a plurality of receiving grooves; and
     a ramp adapted to fit in at least one of said receiving grooves, said ramp causing said user's lower jaw to extend forward with respect to said user.

2. The dental device of claim 1, wherein said receiving grooves are oriented such that the amount of forward extension of the user's lower jaw depends on which receiving groove or grooves said ramp fits in.

3. The dental device of claim 1, and further comprising a shim, said shim being inserted in said slot.

4. The dental device of claim 1, and further comprising a set screw, said set screw operable to adjust the position of said base within said slot.

5. The dental device of claim 1, and further comprising breathing channels extending from the device through lips of said user.

6. The dental device of claim 1, wherein said slot is dove-tailed.

7. The dental device of claim 1, and further comprising a lower arch fitting at least some of said user's lower teeth, said ramp directly contacting said lower arch.

8. The dental device of claim 7, wherein said lower arch includes a locking shoulder, and wherein said ramp includes a matching shoulder, such that said user's lower jaw cannot be substantially lowered while said shoulders are engaged.

9. The dental device of claim 1, and further comprising a lower arch fitting at least some of said user's lower teeth, said ramp indirectly contacting said lower arch.

10. The dental device of claim 1, and further comprising a receiving member coupled to said upper arch, said receiving member providing said slot.

11. A dental device, comprising:
    an upper arch fitting at least some of a user's upper teeth, said upper arch including a slot;
    a base adapted to fit in said slot, said base including a drive member; and
    a ramp coupled to said drive member and extending downward from said upper arch, said drive member operable to adjust the position of said ramp, said ramp causing said user's lower jaw to extend forward with respect to said user.

12. The dental device of claim 11, and further comprising breathing channels extending from the device through lips of said user.

13. The dental device of claim 11, wherein said slot is dove-tailed.

14. The dental device of claim 11, and further comprising a lower arch fitting at least some of said user's lower teeth, said ramp directly contacting said lower arch.

15. The dental device of claim 14, wherein said lower arch includes a locking shoulder, and wherein said ramp includes a matching shoulder, such that said user's lower jaw cannot be substantially lowered while said shoulders are engaged.

16. The dental device of claim 11, and further comprising a lower arch fitting at least some of said user's lower teeth, said ramp indirectly contacting said lower arch.

17. The dental device of claim 11, and further comprising a receiving member coupled to said upper arch, said receiving member providing said slot.

18. A dental device, comprising:

an upper arch fitting at least some of a user's upper teeth;

a lower arch fitting at least some of said user's lower teeth;

a drive member coupled to said upper arch; and a ramp coupled to said drive member and extending downward from said upper arch, said drive member operable to adjust the position of said ramp, said ramp operable to contact said lower arch, said ramp causing said user's lower jaw to extend forward with respect to said user in response to said contact.

19. The dental device of claim 18, and further comprising breathing channels extending from the device through lips of said user.

20. The dental device of claim 18, wherein said ramp directly contacts said lower arch.

21. A dental device, comprising:

an upper arch fitting at least some of a user's upper teeth;

a drive member coupled to said upper arch;

a ramp coupled to said drive member and extending downward from said upper arch, said drive member operable to adjust the position of said ramp, said ramp causing said user's lower law to extend forward with respect to said user; and a lower arch fitting at least some of said user's lower teeth, said ramp directly contacting said lower arch, wherein said lower arch includes a locking shoulder, and wherein said ramp includes a matching shoulder, such that said user's lower jaw cannot be substantially lowered while said shoulders are engaged.

22. The dental device of claim 18, wherein said ramp indirectly contacts said lower arch.

* * * * *